United States Patent
Wilson

(10) Patent No.: US 10,646,539 B2
(45) Date of Patent: May 12, 2020

(54) METHODS AND COMPOSITIONS FOR THE TREATMENT OF NEUROPATHY AND HYPERALGESIA

(71) Applicant: STEALTH BIOTHERAPEUTICS CORP, Monaco (MC)

(72) Inventor: D. Travis Wilson, Newton, MA (US)

(73) Assignee: STEALTH BIOTHERAPEUTICS CORP, Monaco (MC)

( * ) Notice: Subject to any disclaimer, the term of this patent is extended or adjusted under 35 U.S.C. 154(b) by 0 days.

(21) Appl. No.: 16/390,799

(22) Filed: Apr. 22, 2019

(65) Prior Publication Data

US 2019/0343913 A1 Nov. 14, 2019

Related U.S. Application Data

(63) Continuation of application No. 15/488,697, filed on Apr. 17, 2017, now Pat. No. 10,279,008, which is a continuation of application No. 14/388,705, filed as application No. PCT/US2013/034647 on Mar. 29, 2013, now Pat. No. 9,636,378.

(60) Provisional application No. 61/618,428, filed on Mar. 30, 2012.

(51) Int. Cl.

| | |
|---|---|
| *A61K 38/07* | (2006.01) |
| *A61K 38/08* | (2019.01) |
| *A61K 33/243* | (2019.01) |
| *A61K 31/137* | (2006.01) |
| *A61K 31/185* | (2006.01) |
| *A61K 31/337* | (2006.01) |
| *A61K 31/366* | (2006.01) |
| *A61K 31/4245* | (2006.01) |
| *A61K 31/4748* | (2006.01) |
| *A61K 31/55* | (2006.01) |
| *A61K 31/7042* | (2006.01) |

(52) U.S. Cl.
CPC ............ *A61K 38/07* (2013.01); *A61K 31/137* (2013.01); *A61K 31/185* (2013.01); *A61K 31/337* (2013.01); *A61K 31/366* (2013.01); *A61K 31/4245* (2013.01); *A61K 31/4748* (2013.01); *A61K 31/55* (2013.01); *A61K 31/7042* (2013.01); *A61K 33/243* (2019.01); *A61K 38/08* (2013.01)

(58) Field of Classification Search
None
See application file for complete search history.

(56) References Cited

U.S. PATENT DOCUMENTS

| | | | |
|---|---|---|---|
| 5,760,001 | A | 6/1998 | Girten et al. |
| 7,718,620 | B2 * | 5/2010 | Szeto ............... A61K 38/03 514/15.1 |
| 2002/0151465 | A1 | 10/2002 | Messing et al. |
| 2009/0253641 | A1 | 10/2009 | Neufer et al. |

FOREIGN PATENT DOCUMENTS

| | | |
|---|---|---|
| JP | 6317324 B | 4/2018 |
| WO | WO-20051072295 A2 | 8/2005 |
| WO | WO-2011/106717 | 9/2011 |
| WO | WO 2013/100633 A1 | 7/2013 |
| WO | WO 2013/149172 | 10/2013 |

OTHER PUBLICATIONS

Decision of Rejection issued on Chinese Appl. 201380023997.6, dated Dec. 26, 2016, English Translation.
Examination Report issued on Australian Application 2013237827, dated Dec. 20, 2016.
Extended Search Report issued on EP Application 16192386.7, dated Mar. 22, 2017.
Extended Search Report received for European Patent Application No. 13769696.9 dated Sep. 21, 2015, 9 pages.
Ferrari, Luiz F. et al., "Role of Drp1, a Key Mitochondrial Fission Protein, in Neuropathic Pain," J of Neuroscience, (Aug. 3, 2011), vol. 31, pp. 11404-11410.
Fidanboylu, Mehrnet et al., "Global Inhibition of Reactive Oxygen Species (ROS) Inhibits Paclitaxel-Induced Painful Peripheral Neuropathy," PLOS One, (Sep. 2011), vol. 6, Issue 9, pp. 1-11.
First Office Action received in Chinese Patent Application No. 201380023997.6 dated May 27, 2015, 15 pages.
International Search Report and Written Opinion received in International Application No. PCT/US2013/034647 dated Jul. 10, 2013, 9 pages.
Joseph, Elizabeth K. et al., "Oxaliplatin Acts on IB4-Positive Nociceptors to Induce and Oxidative Stress-Dependent Acute Painful Peripheral Neuropathy," The Journal of Pain, (May 2008), vol. 9, Issue 5, pp. 463-472.
JPN. J Phar m. Palliat Care Sci, vol. 4, 2011, pp. 1-13 (English translation not available).
Kim, Hee Kee et al., "Reactive oxygen species (ROS) play an important role in a rat model of neuropathic pain," PAIN, (2004), vol. 111, pp. 116-124.
Li, Jianqiao et al., "Mitochondria-targeted antioxidant peptide SS31 attenuates high glucose-induced injury on human retinal endothelial cells," Biochem. & Biophys. Res. Commun., (2011), 404, pp. 349-356.
Office Action issued on JP Application 2015-503653, dated Nov. 30, 2016,English translation.

(Continued)

*Primary Examiner* — Joanne Hama
*Assistant Examiner* — Jon M Lockard
(74) *Attorney, Agent, or Firm* — Foley & Lardner LLP

(57) ABSTRACT

The disclosure relates to methods for treating a subject suffering from hyperalgesia caused by drug-induced neuropathy by administering to the subject an effective amount of an aromatic-cationic peptide. The disclosure also relates to methods for protecting a subject from hyperalgesia caused by drug-induced neuropathy by administering an effective amount of an aromatic-cationic peptide to a subject at risk for developing the condition.

20 Claims, 2 Drawing Sheets

(56) References Cited

OTHER PUBLICATIONS

Second Office Action received for Chinese Patent Application No. 201380023997.6 dated Feb. 23, 2016, 18 pages—with English translation.
Shimoyama, Megumi et al., "Superior Analgesic Effect of H-Dmt-D-Arg-Phe-Lys-NH2 ([Dmt1]DALDA), a Multifunctional Opioid Peptide, Compared to Morphine in a Rat Model of Neuropathic Pain," Chemical Biology & Drug Design, (2012), vol. 80, issue 5, pp. 771-774.
Zhao, Kesheng et. al., "Cell-permeable Peptide Antioxidants Targeted to Inner Mitochondrial Membrane inhibit Mitochondrial Swelling, Oxidative Cell Death, and Reperfusion Injury," J Biel Chem., (Aug. 2004), vol. 279, No. 33, pp. 34682-34690.
Reexamination Notification issued on Chinese Application 201380023997.6, dated Dec. 4, 2017.
Final Rejection in JP Patent Application No. 2018-063574 dated Nov. 25, 2019 (6 pages) (with English translation).

* cited by examiner

METHODS AND COMPOSITIONS FOR THE TREATMENT OF NEUROPATHY AND HYPERALGESIA

CROSS-REFERENCE TO RELATED APPLICATIONS

This application is a Continuation of U.S. application Ser. No. 15/488,697, filed Apr. 17, 2017, now U.S. Pat. No. 10,279,008, which is a Continuation of U.S. application Ser. No. 14/388,705, filed Sep. 26, 2014, now U.S. Pat. No. 9,636,378, which is the U.S. National Stage of International Application No. PCT/US2013/034647, with an international filing date of Mar. 29, 2013, which claims priority to U.S. Provisional Application No. 61/618,428, filed Mar. 30, 2012, the contents of which are hereby incorporated by reference in their entireties.

TECHNICAL FIELD

The present technology relates generally to compositions for preventing or treating neuropathy comprising an aromatic-cationic peptide and methods for using the same.

BACKGROUND

The following description is provided to assist the understanding of the reader. None of the information provided or the references cited are admitted to be prior art to the present technology.

Chemotherapy-induced peripheral neuropathy results in patient suffering and limits the scope treatment with potentially useful anti-cancer drugs. Vinca alkaloids, such as vincristine and vinblastine, have significant efficacy in the treatment of malignant tumors. However, these agents are highly neurotoxic, frequently causing painful peripheral neuropathies that limit the dose and duration of use in cancer treatment. These side effects are dose and time dependent, often with latencies of days to weeks, and may be cumulative with toxicities associated with other drugs used in combination with chemotherapeutic agents.

SUMMARY

The present disclosure provides compositions and methods for treating or preventing neuropathy or hyperalgesia comprising administering an aromatic-cationic peptide to a subject in need thereof.

In one aspect, the present disclosure provides a method for treating peripheral neuropathy or hyperalgesia in a subject in need thereof, comprising administering to the subject an effective amount of a peptide having the formula D-Arg-2'6'-dimethyltyrosine-Lys-Phe-NH$_2$. In some embodiments, the peripheral neuropathy or hyperalgesia is drug-induced.

In some embodiments, the drug is a chemotherapeutic agent. In some embodiments, the chemotherapeutic agent is procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, thioguanine, or vincristine. In some embodiments, the chemotherapeutic agent is vincristine.

In some embodiments, the peptide is administered simultaneous with the drug. In some embodiments, the peptide is administered subsequent to the drug. In some embodiments, the peripheral neuropathy causes hyperalgesia. In some embodiments, the subject is a human. In some embodiments, the peptide is administered intravenously, orally, subcutaneously, transdermally, intraperitoneally, or topically.

In one aspect, the present disclosure provides a method for preventing hyperalgesia in a subject in need thereof, comprising administering to the subject an effective amount of a peptide having the formula D-Arg-2'6'-dimethyltyrosine-Lys-Phe-NH$_2$. In some embodiments, the hyperalgesia is drug-induced. In some embodiments, the drug is a chemotherapeutic agent.

In some embodiments, the chemotherapeutic agent is procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, thioguanine, or vincristine. In some embodiments, the chemotherapeutic agent is vincristine.

In some embodiments, the peptide is administered simultaneous with the drug. In some embodiments, the peptide is administered subsequent to the drug. In some embodiments, the peptide is administered prior the onset of hyperalgesia. In some embodiments, the subject is a human. In some embodiments, the peptide is administered intravenously, orally, subcutaneously, transdermally, intraperitoneally, intrathecally intramuscularly, intranasally, bucally, sublingually, translingually, or topically.

In one aspect, the present disclosure provides a composition for treating or preventing hyperalgesia in a subject in need thereof, comprising an effective amount of a peptide having the formula D-Arg-2'6'-dimethyltyrosine-Lys-Phe-NH$_2$. In some embodiments, the hyperalgesia is drug-induced.

In some embodiments, the drug is a chemotherapeutic agent. In some embodiments, the chemotherapeutic agent is procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, thioguanine, or vincristine. In some embodiments, the chemotherapeutic agent is vincristine.

In some embodiments, the peptide is administered simultaneous with the drug. In some embodiments, the peptide is administered subsequent to the drug. In some embodiments, the peptide is administered prior the onset of hyperalgesia. In some embodiments, the subject is a human. In some embodiments, the peptide is administered intravenously, orally, subcutaneously, transdermally, intraperitoneally, intrathecally intramuscularly, intranasally, bucally, sublingually, translingually, or topically.

In one embodiment, the peptide is defined by formula I:

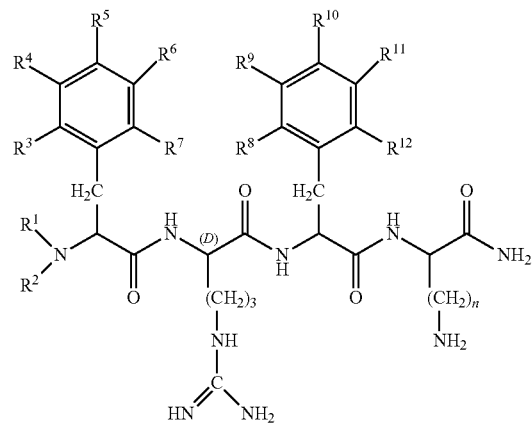

wherein R$^1$ and R$^2$ are each independently selected from
(i) hydrogen;
(ii) linear or branched C$_1$-C$_6$ alkyl;

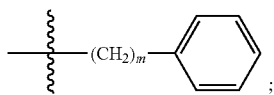

where m = 1-3

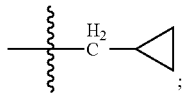

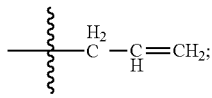

$R^3$, $R^4$, $R^5$, $R^6$, $R^7$, $R^8$, $R^9$, $R^{10}$, $R^{11}$ and $R^{12}$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

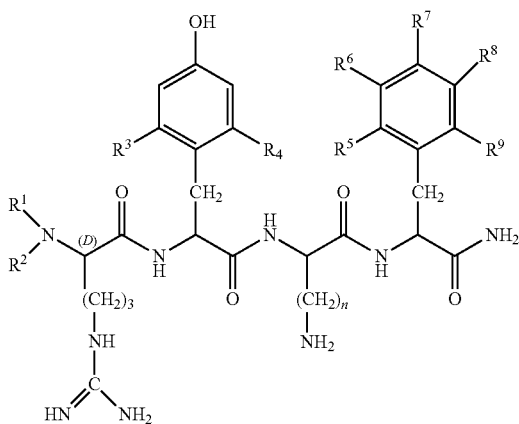

wherein $R^1$ and $R^2$ are each independently selected from
  (i) hydrogen;
  (ii) linear or branched $C_1$-$C_6$ alkyl;

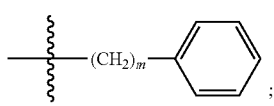

where m = 1-3

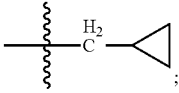

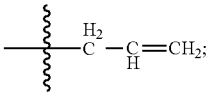

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
$R^5$, $R^6$, $R^7$, $R^8$, and $R^9$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

DETAILED DESCRIPTION

Figure 1:
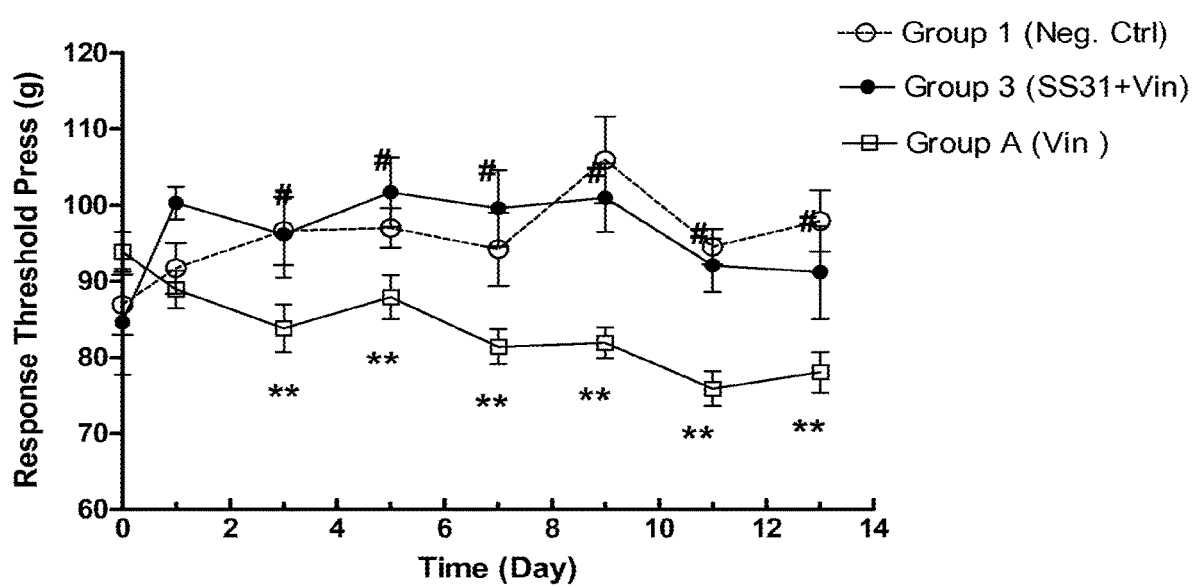
FIG. 1 is a chart showing that D-Arg-2'6'-dimethyltyrosine-Lys-Phe-$NH_2$ is effective in the prevention of vincristine-induced hyperalgesia in rats. # p>0.05 for the comparison of Groups 1 and 3; **p<0.01 for the comparison of Groups 1 and A.

The present disclosure is based on the surprising discovery that certain aromatic-cationic peptides can treat or ameliorate neuropathy and hyperalgesia, including drug-induced neuropathy and hyperalgesia. It is to be appreciated that certain aspects, modes, embodiments, variations, and features of the present technology are described below in various levels of detail in order to provide a substantial understanding of the present technology.

In practicing the present technology, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989);

*DNA Cloning: A Practical Approach*, Vols. I and II, Glover, Ed. (1985); *Oligonucleotide Synthesis*, Gait, Ed. (1984); Nucleic Acid Hybridization, Hames & Higgins, Eds. (1985); Transcription and Translation, Hames & Higgins, Eds. (1984); *Animal Cell Culture, Freshney*, Ed. (1986); Immobilized Cells and Enzymes (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which the present technology belongs.

As used in this specification and the appended claims, the singular forms "a," "an," and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, a neuropathy or one or more conditions associated with a neuropathy, including, but not limited to, hyperalgesia. In the context of therapeutic or prophylactic applications, the amount of a composition administered to the subject will depend on the type and severity of the neuropathy or hyperalgesia and on the characteristics of the individual, such as general health, age, sex, body weight and tolerance to drugs. It will also depend on the degree, severity, and type of the neuropathy or hyperalgesia. The skilled artisan will be able to determine appropriate dosages depending on these and other factors. The compositions can also be administered in combination with one or more additional therapeutic compounds.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with therapeutic uses of the agent. Such interfering materials may include enzymes, hormones and other proteinaceous and nonproteinaceous solutes.

As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may be a neuropathy, or any associated conditions or complications, including, but not limited to, hyperalgesia.

As used herein, "neuropathy" or "peripheral neuropathy" refers generally to damage to nerves of the peripheral nervous system. The term encompasses neuropathy of various etiologies, including, but not limited, to neuropathy caused by, resulting from, or associated with genetic disorders, metabolic/endocrine complications, diabetes, inflammatory diseases, vitamin deficiencies, malignant diseases, and toxicity, such as alcohol, organic metal, heavy metal, radiation, and drug toxicity. As used herein, the term encompasses motor, sensory, mixed sensorimotor, chronic, and acute neuropathy. As used herein the term encompasses mononeuropathy, multiple mononeuropathy, and polyneuropathy.

Illustrative causes of neuropathy include, but are not limited to, neuropathy caused by, resulting from, or associated with diabetes, chemotherapy, trauma, malnutrition, alcoholism, autoimmune diseases, cancer, infectious diseases, kidney disease, liver disease, HIV, AIDS, hypothyroidism, hereditary disorders, and exposure to toxins.

In some embodiments, the present disclosure provides compositions for the treatment or prevention of peripheral neuropathy or the symptoms of peripheral neuropathy. In some embodiments, the peripheral neuropathy is drug-induced peripheral neuropathy. In some embodiments, the peripheral neuropathy is induced by a chemotherapeutic agent. In some embodiments, the chemotherapeutic agent is a vinca alkaloid. In some embodiments, the vinca alkaloid is vincristine. In some embodiments, the symptoms of peripheral neuropathy include hyperalgesia.

As used herein, "hyperalgesia" refers to an increased sensitivity to pain, which may be caused by damage to nociceptors or peripheral nerves (i.e. neuropathy). The term refers to temporary and permanent hyperalgesia, and encompasses both primary hyperalgesia (i.e. pain sensitivity occurring directly in damaged tissues) and secondary hyperalgesia (i.e. pain sensitivity occurring in undamaged tissues surrounding damaged tissues). The term encompasses hyperalgesia caused by, but not limited to, neuropathy caused by, resulting from, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. In some embodiments hyperalgesia is caused by drug-induced peripheral neuropathy.

In some embodiments, the present disclosure provides compositions for the treatment or prevention of hyperalgesia. In some embodiments, the hyperalgesia is drug-induced. In some embodiments, the hyperalgesia is induced by a chemotherapeutic agent. In some embodiments, the chemotherapeutic agent is a vinca alkaloid. In some embodiments, the vinca alkaloid is vincristine.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts, as well as in a voluminous research literature.

As used herein, "prevention" or "preventing" of a disorder or condition with reference to a treatment method (e.g., administration of a compound, such as an aromatic-cationic peptide of the present disclosure), means that the method reduces the occurrence of the disorder or condition in treated subjects relative to an untreated control subjects.

As used herein, the words "protect" or "protecting" refer to decreasing the likelihood and/or risk that the subject treated with a peptide of the present technology will develop a given disease or disorder, or delaying the onset or reducing the severity of one or more symptoms of the disease, disorder or condition, e.g., a neuropathy or associated conditions or complications such as hyperalgesia. Typically, the likelihood of developing the disease or disorder is considered to be reduced if the likelihood is decreased by at least about 10%, at least about 25%, at least about 50%, at least about 75%, at least about 90%, in comparison to the likelihood and/or risk that the same subject untreated with a peptide of the present technology will develop a neuropathy or a hyperalgesia. In some embodiments, the peptides protect a subject against the development of a neuropathy or a hyperalgesia when the peptides are administered after a subject receives a neuropathy-inducing drug, but before the onset of neuropathy or hyperalgesia.

The term "subject" as used herein refers to a member of any vertebrate species. The methods of the presently disclosed subject matter are particularly useful for warm-blooded vertebrates. Provided herein is the treatment of mammals such as humans, as well as those mammals of importance due to being endangered, of economic importance (animals raised on farms for consumption by humans) and/or social importance (animals kept as pets or in zoos) to humans. In some embodiments, the subject is a human.

As used herein, the terms "treating," "treatment," or "alleviation" refer to both therapeutic treatment and prophylactic or preventative measures, wherein the object is to prevent or slow down (lessen) the targeted pathologic condition or disorder. A subject is successfully "treated" for a disease or condition if, after receiving a therapeutic amount of the aromatic-cationic peptides according to the methods described herein, the subject shows observable and/or measurable reduction in or absence of one or more signs and symptoms of a particular disease or condition. For example, for a neuropathy or a hyperalgesia, treatment or prevention may include a reduction frequency, severity, or duration of symptoms, such as pain in the extremities. It is also to be appreciated that the various modes of treatment or prevention of medical conditions as described are intended to mean "substantial", which includes total but also less than total treatment or prevention, and wherein some biologically or medically relevant result is achieved.

Peptides

The aromatic-cationic peptides useful in the present methods are water-soluble and highly polar. Despite these properties, the peptides can readily penetrate cell membranes. The aromatic-cationic peptides useful in the present methods include a minimum of three amino acids, and preferably include a minimum of four amino acids, covalently joined by peptide bonds. The maximum number of amino acids present in the aromatic-cationic peptides of the present methods is about twenty amino acids covalently joined by peptide bonds. In some embodiments, the maximum number of amino acids is about twelve, about nine, or about six. In some embodiments, the number of amino acids present in the peptides is four.

The amino acids of the aromatic-cationic peptides can be any amino acid. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea.

The peptides can optionally contain one or more non-naturally occurring amino acids. The non-naturally occurring amino acids may be L-, dextrorotatory (D), or mixtures thereof. The peptide may have no amino acids that are naturally occurring. Non-naturally occurring amino acids are those amino acids that typically are not synthesized in normal metabolic processes in living organisms, and do not naturally occur in proteins. In addition, the non-naturally occurring amino acids are not recognized by common proteases.

The non-naturally occurring amino acid can be present at any position in the peptide. For example, the non-naturally occurring amino acid can be at the N-terminus, the C-terminus, or at any position between the N-terminus and the C-terminus. The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid. Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant, and in some embodiments, insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides may have less than five, less than four, less than three, less than two contiguous L-amino acids recognized by common proteases, irrespective of whether the amino acids are naturally or non-naturally occurring. If the peptide contains protease sensitive sequences of amino acids, at least one of the amino acids may be a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

In suitable embodiments, the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid. Typically, a peptide has a positively charged N-terminal amino group and a negatively charged C-terminal carboxyl group. The charges cancel each other out at physiological pH.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($2p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges. In suitable embodiments, the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

In one embodiment, the aromatic-cationic peptides have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, may be amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present technology may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following exemplary peptides:

Lys-D-Arg-Tyr-NH₂
Phe-D-Arg-His
D-Tyr-Trp-Lys-NH₂
Trp-D-Lys-Tyr-Arg-NH₂
Tyr-His-D-Gly-Met
Phe-Arg-D-His-Asp
Tyr-D-Arg-Phe-Lys-Glu-NH₂
Met-Tyr-D-Lys-Phe-Arg
D-His-Glu-Lys-Tyr-D-Phe-Arg
Lys-D-Gln-Tyr-Arg-D-Phe-Trp-NH₂
Phe-D-Arg-Lys-Trp-Tyr-D-Arg-His
Gly-D-Phe-Lys-Tyr-His-D-Arg-Tyr-NH₂
Val-D-Lys-His-Tyr-D-Phe-Ser-Tyr-Arg-NH₂
Trp-Lys-Phe-D-Asp-Arg-Tyr-D-His-Lys
Lys-Trp-D-Tyr-Arg-Asn-Phe-Tyr-D-His-NH₂
Thr-Gly-Tyr-Arg-D-His-Phe-Trp-D-His-Lys
Asp-D-Trp-Lys-Tyr-D-His-Phe-Arg-D-Gly-Lys-NH₂
D-His-Lys-Tyr-D-Phe-Glu-D-Asp-D-His-D-Lys-Arg-Trp-NH₂
Ala-D-Phe-D-Arg-Tyr-Lys-D-Trp-His-D-Tyr-Gly-Phe
Tyr-D-His-Phe-D-Arg-Asp-Lys-D-Arg-His-Trp-D-His-Phe
Phe-Phe-D-Tyr-Arg-Glu-Asp-D-Lys-Arg-D-Arg-His-Phe-NH₂
Phe-Try-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH₂
Arg-D-Leu-D-Tyr-Phe-Lys-Glu-D-Lys-Arg-D-Trp-Lys-D-Phe-Tyr-D-Arg-Gly
D-Glu-Asp-Lys-D-Arg-D-His-Phe-Phe-D-Val-Tyr-Arg-Tyr-D-Tyr-Arg-His-Phe-NH₂
Asp-Arg-D-Phe-Cys-Phe-D-Arg-D-Lys-Tyr-Arg-D-Tyr-Trp-D-His-Tyr-D-Phe-Lys-Phe
His-Tyr-D-Arg-Trp-Lys-Phe-D-Asp-Ala-Arg-Cys-D-Tyr-His-Phe-D-Lys-Tyr-His-Ser-NH₂
Gly-Ala-Lys-Phe-D-Lys-Glu-Arg-Tyr-His-D-Arg-D-Arg-Asp-Tyr-Trp-D-His-Trp-His-D-Lys-Asp
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂

In some embodiments, peptides are those peptides which have a tyrosine residue or a tyrosine derivative. Suitable derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltryosine (Hmt).

In one embodiment, the peptide has the formula Tyr-D-Arg-Phe-Lys-$NH_2$. Tyr-D-Arg-Phe-Lys-$NH_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-$NH_2$ can be a modified derivative of tyrosine such as in 2',6'-dimethyltyrosine to produce the compound having the formula 2',6'-Dmt-D-Arg-Phe-Lys-$NH_2$.

In a suitable embodiment, the amino acid residue at the N-terminus is arginine. An example of such a peptide is D-Arg-2'6'Dmt-Lys-Phe-$NH_2$. In another embodiment, the amino acid at the N-terminus is phenylalanine or its derivative. Derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp). An example of such a peptide is Phe-D-Arg-Phe-Lys-$NH_2$. In one embodiment, the amino acid sequence of 2',6'-Dmt-D-Arg-Phe-Lys-$NH_2$ is rearranged such that Dmt is not at the N-terminus. An example of such an aromatic-cationic peptide has the formula D-Arg-2'6'Dmt-Lys-Phe-$NH_2$.

In yet another embodiment, the aromatic-cationic peptide has the formula Phe-D-Arg-Dmt-Lys-$NH_2$. Alternatively, the N-terminal phenylalanine can be a derivative of phenylalanine such as 2',6'-dimethylphenylalanine (2'6'Dmp). Tyr-D-Arg-Phe-Lys-$NH_2$ containing 2',6'-dimethylphenylalanine at amino acid position one has the formula 2',6'-Dmp-D-Arg-Dmt-Lys-$NH_2$.

Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide. Examples of peptides include, but are not limited to, the aromatic-cationic peptides shown in Table 5.

TABLE 5

Examples of Aromatic-Cationic Peptides

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| D-Arg | Dmt | Lys | Phe | $NH_2$ |
| D-Arg | Dmt | Lys | Phe | $NH_2$ |
| D-Arg | Dmt | Lys | Phe | $NH_2$ |
| D-Arg | Dmt | Lys | Phe | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Phe | Lys | $NH_2$ |
| Phe | D-Arg | Phe | Lys | $NH_2$ |
| Phe | D-Arg | Phe | Lys | $NH_2$ |
| Phe | D-Arg | Phe | Lys | $NH_2$ |
| Phe | D-Arg | Dmt | Lys | $NH_2$ |
| Phe | D-Arg | Dmt | Lys | $NH_2$ |
| Phe | D-Arg | Dmt | Lys | $NH_2$ |
| Phe | D-Arg | Dmt | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexylalanine

Under certain circumstances, it may be advantageous to use a peptide that also has opioid receptor agonist activity. Examples of mu-opioid analogs include, but are not limited to, the aromatic-cationic peptides shown in Table 6.

TABLE 6

Aromatic-Cationic Peptides with Opioid Receptor Agonist Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| Tyr | D-Arg | Phe | Lys | $NH_2$ |
| 2'6'Dmt | D-Arg | Phe | Lys | $NH_2$ |
| 2'6'Dmt | D-Arg | Phe | Lys | $NH_2$ |
| 2'6'Dmt | D-Arg | Phe | Lys-$NH(CH_2)_2$—NH-dns | $NH_2$ |
| 2'6'Dmt | D-Arg | Phe | Lys-$NH(CH_2)_2$—NH-atn | $NH_2$ |
| 2'6'Dmt | D-Arg | Phe | dnsLys | $NH_2$ |
| 2'6'Dmt | D-Cit | Phe | Lys | $NH_2$ |

TABLE 6-continued

Aromatic-Cationic Peptides with Opioid Receptor Agonist Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| 2'6'Dmt | D-Arg | 2'6'Dmt | Lys | $NH_2$ |
| Tyr | D-Lys | Phe | Dap | $NH_2$ |
| Tyr | D-Lys | Phe | Arg | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin The amino acids of the peptides shown in Tables 5 and 6 may be in either the L- or the D-configuration.

Synthesis of the Peptides

The peptides useful in the methods of the present technology may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis," *Methods Enzymol.*, 289, Academic Press, Inc, New York (1997).

Neuropathy and Hyperalgesia

The aromatic-cationic peptides described herein are useful in treating or preventing neuropathy or hyperalgesia. In some embodiments, the aromatic-cationic peptides may be administered to a subject following the onset of neuropathy or hyperalgesia. Thus, the term "treatment" is used herein in its broadest sense and refers to use of an aromatic-cationic peptide for a partial or complete cure of the neuropathy or hyperalgesia, a reduction or amelioration of signs or symptoms, and/or a reduction of severity of signs or symptoms.

In other embodiments, the aromatic-cationic peptides of the present technology may be administered to a subject before the onset of neuropathy or hyperalgesia in order to prevent, protect against and/or provide prophylaxis for neuropathy or hyperalgesia. It is also contemplated that the compounds may be administered to a subject at risk of developing neuropathy or hyperalgesia.

The term "peripheral neuropathy" refers generally to damage to nerves of the peripheral nervous system. The term encompasses neuropathy of various etiologies, including, but not limited to, acquired neuropathies, hereditary neuropathies, and idiopathic neuropathies. Illustrative acquired neuropathies include, but are not limited to, e.g., neuropathies caused by, resulting from, or otherwise associated with trauma, metabolic/endocrine disorders (e.g., diabetes), inflammatory diseases, infectious diseases, vitamin deficiencies, malignant diseases, and toxicity, such as alcohol, organic metal, heavy metal, radiation, and drug toxicity. As used herein, the "peripheral neuropathy" encompasses motor, sensory, mixed sensorimotor, chronic, and acute neuropathy. As used herein the term encompasses mononeuropathy, multiple mononeuropathy, and polyneuropathy.

Illustrative causes of neuropathy include, but are not limited to, neuropathy caused by, resulting from, or associated with diabetes, chemotherapy, trauma, malnutrition, alcoholism, autoimmune diseases, cancer, infectious diseases, kidney disease, liver disease, HIV, AIDS, hypothyroidism, hereditary disorders, and exposure to toxins.

Drug toxicity causes multiple forms of peripheral neuropathy, with the most common being axonal degeneration. A notable exception is that of perhexiline, a prophylactic anti-anginal agent that can cause segmental demyelination, a localized degeneration of the insulating layer around some nerves.

Peripheral neuropathies usually present sensory symptoms initially, and often progress to motor disorders. Most drug-induced peripheral neuropathies are purely sensory or mixed sensorimotor defects. An exception is that of Dapzone, which causes an almost exclusively motor neuropathy.

Drug-induced peripheral neuropathy, including, for example, chemotherapy-induced peripheral neuropathy can cause a variety of dose-limiting neuropathic conditions, including 1) myalgias, 2) painful burning paresthesis, 3) glove-and-stocking sensory neuropathy, and 4) hyperalgia and allodynia. Hyperalgia refers to hypersensitivity and pain caused by stimuli that is normally only mildly painful or irritating. Allodynia refers to hypersensitivity and pain caused by stimuli that is normally not painful or irritating.

The term "hyperalgesia" refers to an increased sensitivity to pain, which may be caused by damage to nociceptors or peripheral nerves (i.e. neuropathy). The term refers to temporary and permanent hyperalgesia, and encompasses both primary hyperalgesia (i.e. pain sensitivity occurring directly in damaged tissues) and secondary hyperalgesia (i.e. pain sensitivity occurring in undamaged tissues surrounding damaged tissues). The term encompasses hyperalgesia caused by peripheral neuropathy, including, but not limited to, neuropathy caused by, resulting from, or associated with genetic disorders, metabolic/endocrine complications, inflammatory diseases, vitamin deficiencies, malignant diseases, and toxicity, such as alcohol, organic metal, heavy metal, radiation, and drug toxicity. In some embodiments hyperalgesia is caused by drug-induced peripheral neuropathy.

In some embodiments, the present disclosure provides compositions for the treatment or prevention of hyperalgesia. In some embodiments, the hyperalgesia is drug-induced. In some embodiments, the hyperalgesia is induced by a chemotherapeutic agent. In some embodiments, the chemotherapeutic agent is a vinca alkaloid. In some embodiments, the vinca alkaloid is vincristine.

A wide variety of pharmaceuticals are known to cause drug-induced neuropathy, including, but not limited to, e.g., anti-microbials, anti-neoplastic agents, cardiovascular drugs, hypnotics and psychotropics, anti-rheumatics, and anti-convulsants.

Illustrative anti-microbials known to cause neuropathy include, but are not limited to, e.g., isoniazid, ethambutol, ethionamide, nitrofurantoin, metronidazole, ciprofloxacin, chloramphenicol, thiamphenicol, diamines, colistin, streptomycin, nalidixic acid, clioquinol, sulphonamides, amphotericin, penicillin.

Illustrative anti-neoplastic agents known to cause neuropathy include, but are not limited to, e.g., procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, and thioguanine. Vinca alkaloids, such as vincristine, are known to be particularly neurotoxic.

Illustrative cardiovascular drugs known to cause neuropathy include, but are not limited to, e.g., propranolol, perhexiline, hydrallazine, amiodarone, disopyramide, and clofibrate.

Illustrative hypnotics and psychotropics known to cause neuropathy include, but are not limited to, e.g., phenelzine, thalidomide, methaqualone, glutethimide, amitriptyline, and imipramine.

Illustrative anti-rheumatics known to cause neuropathy include, but are not limited to, e.g., gold, indomethacin, colchicine, chloroquine, and phenyl butazone.

Illustrative anti-convulsants known to cause neuropathy include, but are not limited to, e.g., phenytoin.

Other drugs known to cause neuropathy include, but are not limited to, e.g., calcium carbimide, sulfoxone, ergotamine, propylthiouracil, sulthaime, chlorpropamide, methysergide, phenytoin, disulfiram, carbutamide, tolbutamide, methimazole, dapsone, and anti-coagulants.

Methods of Prevention and Treatment

General.

The aromatic-cationic peptides described herein are useful to prevent, ameliorate, or treat disease. Specifically, the disclosure provides for methods of treating or preventing neuropathy or hyperalgesia, comprising administering to a subject in need thereof an effective amount of an aromatic-cationic peptide. In some embodiments, the peptide is D-Arg-2'6'-dimethyltyrosine-Lys-Phe-NH$_2$. In some embodiments, the neuropathy or hyperalgesia is drug-induced. In some embodiments, the drug-induced neuropathy or hyperalgesia is caused by administration of a chemotherapeutic agent. In some embodiments, the chemotherapeutic agent is a vinca alkaloid. In some embodiments, the vinca alkaloid is vincristine.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment of neuropathy or hyperalgesia. In various embodiments, in vitro assays can be performed with representative cells of the type(s) involved in the subject's disorder, to determine whether a given aromatic-cationic peptide-based therapeutic exerts the desired effect upon the cell type(s). Compounds for use in therapy can be tested in suitable animal model systems including, but not limited to, rats, mice, chicken, cows, monkeys, rabbits, and the like, prior to testing in human subjects. Similarly, for in vivo testing, any of the animal model system known in the art can be used prior to administration to human subjects. Conditions associated with neuropathy or hyperalgesia, and the efficacy of aromatic-cationic peptides in preventing or treating such, can be readily detected, for example, by measuring the sensitivity of animal subjects to pain stimuli, such as by the methods outlined in Examples 1 and 2 below.

Prophylactic Methods.

In one aspect, the present technology provides a method for preventing neuropathy or hyperalgesia in a subject, or symptoms associated with neuropathy or hyperalgesia comprising administering to the subject an effective amount of an aromatic-cationic peptide such as D-Arg-2'6'-dimethyltyrosine-Lys-Phe-NH$_2$. In some embodiments, the peptide is administered simultaneous with one or more therapeutic drugs in order to treat or prevent drug-induced neuropathy or hyperalgesia. In some embodiments, the peptide is administered prior to one or more therapeutic drugs in order to treat or prevent drug-induced neuropathy or hyperalgesia. In some embodiments the peptide is administered prior to, and/or simultaneous with, one or more therapeutic drugs in order to treat or prevent drug-induced neuropathy or hyperalgesia. In some embodiments, the peptide is administered simultaneous to and/or subsequent to the drug in order to treat or prevent neuropathy or hyperalgesia. In some embodiments, the peptide is administered subsequent to the administration of one or more therapeutic agents, but prior to the onset of neuropathy or hyperalgesia or symptoms of neuropathy or hyperalgesia.

Subjects at risk for drug-induced neuropathy or hyperalgesia may be identified by various diagnostic or prognostic methods known in the art. For example, subjects with a history of drug-induced neuropathy or hyperalgesia, or a family history of neuropathy or hyperalgesia, may be assessed as being at risk for the development of neuropathy or hyperalgesia. Additionally or alternatively, subjects administered multiple therapeutic agents, or administered one or more therapeutic agents for an extended period of time, may be assessed as being at risk for the development of neuropathy or hyperalgesia.

Therapeutic Methods.

Another aspect of the technology includes methods of reducing the symptoms associated with neuropathy or hyperalgesia in a subject for therapeutic purposes. In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease. As such, the present technology provides methods of treating an individual afflicted with neuropathy or hyperalgesia or symptoms associated with neuropathy or hyperalgesia.

In one embodiment, administration of an aromatic-cationic peptide such as D-Arg-2'6'-dimethyltyrosine-Lys-Phe-NH$_2$ to a subject exhibiting one or more symptoms of neuropathy or hyperalgesia will cause an improvement in one or more of those medical conditions. For instance, a subject may exhibit at least about 5%, at least about 10%, at least about 20%, or at least about 50% improvement in the clinical symptoms of neuropathy or hyperalgesia compared to the symptoms as assessed prior to administration of the aromatic-cationic peptide. In some embodiments, a subject may exhibit at least about 5%, at least about 10%, at least about 20%, or at least about 50% reduction in the duration of symptoms of neuropathy or hyperalgesia. In some embodiments, a subject may exhibit at least about 5%, at least about 10%, at least about 20%, or at least about 50% reduction in the frequency of symptoms of neuropathy or hyperalgesia. In some embodiments, a subject may exhibit at least about 5%, at least about 10%, at least about 20%, or at least about 50% reduction in the severity of symptoms of neuropathy or hyperalgesia. In some embodiments, the subject may show improvement in one or more of the duration, frequency, or severity of symptoms of neuropathy or hyperalgesia.

Combination Therapies

The present disclosure contemplates combination therapies comprising the administration of an aromatic-cationic peptide such as D-Arg-2'6'-dimethyltyrosine-Lys-Phe-NH$_2$ with one or more additional therapeutic regimens. In some embodiments, the additional therapeutic regimens are directed to the treatment or prevention of neuropathy or hyperalgesia or symptoms associated with neuropathy or hyperalgesia. In some embodiments, the additional therapeutic regimens are directed to the treatment or prevention of diseases or medical conditions unrelated to neuropathy or hyperalgesia. In some embodiments, the additional therapeutic regimens include regimens directed to the treatment or prevention of neuropathy or hyperalgesia or symptoms associated with neuropathy or hyperalgesia, in addition to diseases, medical conditions, or symptoms unrelated to neuropathy or hyperalgesia or symptoms associated with neuropathy or hyperalgesia. In some embodiments, the additional therapeutic regimens comprise administration of one or more drugs, including, but not limited to, anti-microbials, anti-neoplastic agents, cardiovascular drugs, hypnotics and psychotropics, anti-rheumatics, and anti-convulsants. In embodiments, the additional therapeutic regimens comprise non-pharmaceutical therapies, including, but not limited to, dietary and lifestyle management.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, such as a human. When used in vivo for therapy, the aromatic-cationic peptides of the present technology are administered to the subject in effective amounts (i.e., amounts that have desired therapeutic effect). They will normally be administered intravenously, orally, subcutaneously, transdermally, intraperitoneally, intrathecally intramuscularly, intranasally, bucally, sublingually, translingually, or topically. The dose and dosage regimen will depend upon the severity of neuropathy, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide, such as in a pharmaceutical composition, may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, acetate or trifluoroacetate, and the like.

The aromatic-cationic peptides described herein can be incorporated into pharmaceutical compositions for administration, singly or in combination, to a subject for the treatment or prevention of a disorder or medical condition described herein. Such compositions typically include the active agent and a pharmaceutically acceptable carrier. As used herein the term "pharmaceutically acceptable carrier" includes saline, solvents, dispersion media, coatings, antibacterial and anti-fungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; anti-bacterial agents such as benzyl alcohol or methyl parabens; anti-oxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various anti-bacterial and anti-fungal agents, for example, parabens, chlorobutanol, phenol, ascorbic acid, thiomersal, and the like. In many cases, it will be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In one embodiment, transdermal administration may be performed my iontophoresis.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to other cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present technology, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. In some embodiments, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. Thereafter, the patient can be administered a prophylactic regime.

In some embodiments, a therapeutically effective amount of an aromatic-cationic peptide may be defined as a concentration of peptide at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.001 to about 0.5 mg/kg/h, suitably from about 0.01 to about 0.1 mg/kg/h. In one embodiment, the mid-dose is provided from about 0.1 to about 1.0 mg/kg/h, suitably from about 0.1 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including, but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present technology can be any mammal, including, for example, farm animals, such as sheep, pigs, cows, and horses; pet animals, such as dogs and cats; laboratory animals, such as rats, mice and rabbits. In a some embodiments, the mammal is a human.

EXAMPLES

The present technology is further illustrated by the following examples, which should not be construed as limiting in any way.

Example 1: Use of D-Arg-2'6'-dimethyltyrosine-Lys-Phe-NH$_2$ in the Prevention and Treatment of Drug-Induced Hyperalgesia in Rats This example illustrates the methods and compositions of the present technology in the prevention and treatment of hyperalgesia. The example demonstrates the use of D-Arg-2'6'-dimethyltyrosine-Lys-Phe-NH$_2$ in the prevention and treatment of vincristine-induced hyperalgesia in rats.

Female Sprague Dawley rats were divided randomly into 5 groups (n=10), according to Table 7. Groups 2-4 were administered Vincristine 0.10 mg/kg injected intravenously (i.v.) via tail vein followed by a bolus injection of 0.1 ml PBS vehicle, once daily for 14 days. Group 1 was administered 1 ml/kg PBS vehicle alone according to the same schedule. D-Arg-2'6'-dimethyltyrosine-Lys-Phe-NH$_2$ 10 mg/kg was administered subcutaneously (s.c.) 15 minutes prior to vincristine administration for the full 14-day period (Group 3), or for a period of two weeks beginning at day 15 (Group 4). Group 5 was administered Vincristine 0.10 mg/kg injected i.v. via tail vein, followed by a bolus injection of 0.1 ml PBS vehicle once daily for 28 days, and D-Arg-2'6'-dimethyltyrosine-Lys-Phe-NH$_2$ 10 mg/kg administered s.c. for a period of 14 days beginning at day 15.

TABLE 7

Use of D-Arg-2'6'-dimethyltyrosine-Lys-Phe-NH$_2$ in the Prevention and Treatment of Drug-Induced Hyperalgesia in Rats

| Group | Condition | Treatment* |
|---|---|---|
| 1 | Untreated Control | PBS vehicle |
| 2 | PBS Control | Vincristine + PBS vehicle |
| 3 | D-Arg-2'6'-dimethyltyrosine-Lys-Phe-NH$_2$ | Vincristine + D-Arg-2'6'-dimethyltyrosine-Lys-Phe-NH$_2$ |
| 4 | D-Arg-2'6'-dimethyltyrosine-Lys-Phe-NH$_2$ | (i) Vincristine (14 days) (ii) D-Arg-2'6'-dimethyltyrosine-Lys-Phe-NH$_2$, beginning at day 15 |
| 5 | D-Arg-2'6'-dimethyltyrosine-Lys-Phe-NH$_2$ | (i) Vincristine (28 days) (ii) D-Arg-2'6'-dimethyltyrosine-Lys-Phe-NH$_2$, beginning at day 15 |

Figure 2:
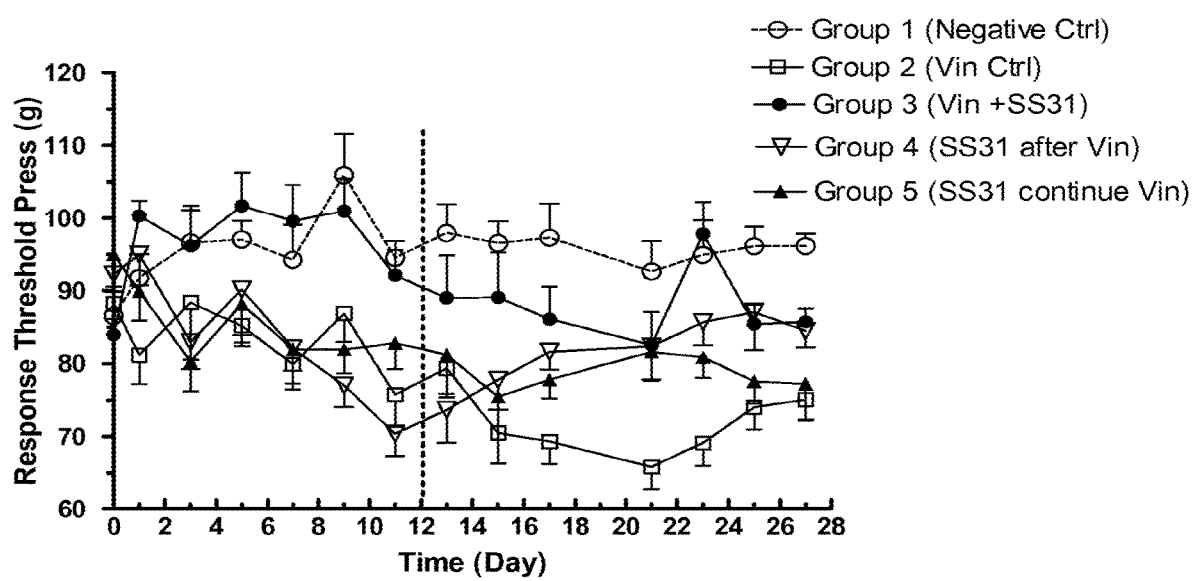
FIG. 2 is a chart showing that D-Arg-2'6'-dimethyltyrosine-Lys-Phe-$NH_2$ is effective in the treatment of vincristine-induced hyperalgesia in rats.

*Vincristine 0.10 mg/kg injected daily i.v.; D-Arg-2'6'-dimethyltyrosine-Lys-Phe-NH$_2$ 10 mg/kg injected daily s.c.; PBS vehicle at pH 7.0; Von Frey test conducted every two days Mechanical nociceptive threshold of paw-withdrawal was measured every two days using an electronic Von Frey test. Results are shown in FIG. 1 and FIG. 2 as means±SEM. One-way ANOVA with post-hoc test or t-test were used to assess the statistical significance, with $p<0.05$ is considered statistically significant. In FIG. 1, data for subjects receiving vincristine in the absence of simultaneous D-Arg-2'6'-dimethyltyrosine-Lys-Phe-NH$_2$ (Groups 2, 4, 5) is shown collectively as "Group A."

Results—

As shown in FIG. 1, subjects administered vincristine for a period of 14 days (Group A) showed a decrease in pain threshold compared to a vehicle-only control (Group 1). By contrast, the pain threshold of subjects administered D-Arg-2'6'-dimethyltyrosine-Lys-Phe-NH$_2$ together with vincristine (Group 3) was not significantly different from the vehicle-only control. This shows that co-administration of D-Arg-2'6'-dimethyltyrosine-Lys-Phe-NH$_2$ together with vincristine prevents vincristine-induced hyperalgesia in mammalian subjects.

As shown in FIG. 2, subjects administered vincristine for a period of 14 days (Groups 2, 4) showed a decrease in pain threshold response compared to a vehicle-only control (Group 1). Following the withdrawal of vincristine, subjects not administered D-Arg-2'6'-dimethyltyrosine-Lys-Phe-NH$_2$ continued to show a decline in pain threshold, reaching a low point at day 21, and showed a moderate improvement beginning at day 22 (Group 2). By contrast, subjects administered D-Arg-2'6'-dimethyltyrosine-Lys-Phe-NH$_2$ following the withdrawal of vincristine showed improved pain threshold as soon as day 15, with continued improvement through day 25 (Group 4). This shows that administration of D-Arg-2'6'-dimethyltyrosine-Lys-Phe-NH$_2$ subsequent to vincristine therapy improves the rate of recovery of a mammalian subject from vincristine-induced hyperalgesia.

As further shown in FIG. 2, subjects administered vincristine in the absence of D-Arg-2'6'-dimethyltyrosine-Lys-Phe-NH$_2$ for a period of 14 days, and then administered vincristine together with D-Arg-2'6'-dimethyltyrosine-Lys-Phe-NH$_2$ for a period of 14 days, showed an arrest of the downward trend in pain threshold evident in the initial 14 day period, followed by an improvement in pain threshold beginning at day 16 (Group 5). This shows that administration of D-Arg-2'6'-dimethyltyrosine-Lys-Phe-NH$_2$ subsequent to the development of vincristine-induced hyperalgesia is effective in halting further progression of the condition and promotes improvement of the condition, even where a subject continues to receive vincristine.

This example shows that aromatic-cationic peptides of the present technology, such as D-Arg-2'6'-dimethyltyrosine-Lys-Phe-NH$_2$, are useful in the prevention and treatment of vincristine-induced hyperalgesia. The results further show that aromatic-cationic peptides of the present technology, such as D-Arg-2'6'-dimethyltyrosine-Lys-Phe-NH$_2$ are useful in the prevention and treatment of drug-induced hyperalgesia generally.

Example 2—Use of D-Arg-2'6'-dimethyltyrosine-Lys-Phe-NH$_2$ in the Treatment of Drug-Induced Hyperalgesia in Humans This example will demonstrate use of the methods and compositions of the present technology in the treatment of hyperalgesia in human subjects. The example will demonstrate the use of D-Arg-2'6'-dimethyltyrosine-Lys-Phe-NH$_2$ in the treatment of vincristine-induced hyperalgesia in humans.

Patients will be recruited to the study as they present in clinic with chronic (>6 months' duration), spontaneous, ongoing, vincristine-related pain. Those enrolled will rate their daily maximum level of pain at 4 or greater on a visual analog scale (VAS). The patients will be screened for their willingness to enroll in the study, and informed consent will be obtained. Healthy subjects will also be recruited for collection of comparison data. No subjects in either the patient or comparison group will have known risk factors for any other cause of peripheral neuropathy, including diabetes, AIDS, chronic alcoholism, or previous radiation exposure.

After a focused interview about the history of the patient's cancer and treatment, the patient will be asked to describe sensory symptoms by choosing from a list of ideal type word descriptors. Ongoing and daily maximum pain intensity will be rated on a VAS with prompts of "no pain" at the bottom and "most imaginable" at the top. The areas of pain and sensory disturbances will be drawn by each patient on a standardized body map. Similar to previous observations in patients treated with paclitaxel, subjects with vincristine-induced peripheral neuropathy are predicted to identify the following three zones of sensation:

a) The painful area: The zone of ongoing pain located on the tips of the fingers and/or toes. The tip of the index finger is expected to be involved in all patients and will be used as the test site in this zone.

b) The border area: Adjacent and proximal to, but distinct from the painful area, represented by nonpainful sensory disturbances and located in the palms and/or soles of the feet. The thenar eminence is expected to be involved in all patients and will be used as the test site in this zone.

c) The nonpainful area: Adjacent and proximal to, but distinct from the border area, reported by the patient to feel "normal." This site is expected to be always proximal to the wrists and/or ankles. Sensory testing will be conducted on the volar surface of the arm.

The tip of the index finger, thenar eminence, and volar forearm, will be tested in normal subjects for comparison. Patients will be specifically queried about the stimuli that provoked pain or caused an exacerbation of ongoing pain in these regions, including the effects that clothing, bed linens, bathing, and normal activities of daily living cause. Each zone will be examined for any physical changes, such as scaling, finger clubbing, and erythema, which will be documented. The areas of sensory disturbance will be physically probed by light touch with a camel hair brush and by manual massage to screen for the presence of allodynia or hyperalgesia.

Touch and Sharpness Detection Thresholds—

Touch detection thresholds will be determined with von Frey monofilaments using the up/down method as previously reported. Starting with a bending force of 0.02 g, each monofilament will be applied to a spot on the skin less than 2 mm in diameter for approximately one second. The force of the filament detected four consecutive times will be assigned as the touch detection threshold. Sharpness detection will be determined using weighted 30-gauge metal cylinders. Briefly, the tip of 30-gauge needles (200 mm diameter) will be filed to produce flat, cylindrical ends and the luers will be fitted to calibrated brass weights with the desired force (100, 200, and 400 mN) level for each stimulus. Each loaded needle will be placed inside a separate 10 cc syringe where it will be able to move freely. Each stimulus will be applied for one second perpendicular to the skin 10 times within each area of interest in a pseudorandom order. The subjects will indicate whether the stimulus is perceived as touch, pressure, sharp, or other. The percentages of each reply will be calculated and then combined into group grand means for comparison. The 50% sharpness detection threshold will be calculated as the weighted needle that caused five or more sharp responses after 10 consecutive stimuli.

Grooved Pegboard Test—

Manual dexterity will be assessed with the grooved pegboard test. Subjects will be instructed to fill a five-by-five slotted pegboard in an ordered fashion and the times for both dominant and non-dominant hands will be recorded.

Thermal Detection Thresholds—

The threshold for heat pain will be determined using the Marstock technique. A radiometer will be used at the outset of testing to ascertain the baseline skin temperature at all testing sites. All tests and measurements will be conducted at room temperature 22° C. Thermal ramps will be applied using a 3.6×3.6 cm Peltier thermode from a baseline temperature of 32° C. Skin heating will be at a ramp of 0.30° C./s, and skin cooling will be at a ramp of −0.5° C./s. Subjects will be instructed to signal when the stimulus is perceived as first becoming warmer and then painfully hot, or as first becoming cooler and then painfully cold. If a subject fails to reach a given threshold before the cutoff temperature of 51.5° C. for the ascending ramp or 3° C. held for 10 seconds in the cooling test, the cutoff values will be assigned for any that are not reached. The final threshold value for each skin sensation in each patient will be determined by averaging the results of three heating and cooling trials.

Statistical Analysis—

The thresholds for touch detection will be compared using nonparametric methods (Wilcoxon's test). The sharpness detection, thermal thresholds, and times in the grooved pegboard tests will be compared using analysis of variance and post hoc comparison of the means with Duncan's multiple range tests. Comparisons of mechanical and thermal thresholds will be performed between healthy subjects and patients for the different areas of the tested skin. Further analyses will be performed between glabrous and volar skin within the patient group. For every comparison performed in the present study, $p<0.05$ will be considered significant.

Following initial assessment of the above criteria, subjects will be divided into four groups:
a) Healthy controls
b) No treatment
c) Vehicle-only placebo, administered s.c., once daily for 14 days
d) D-Arg-2'6'-dimethyltyrosine-Lys-Phe-NH$_2$ at 1-100 mg/kg (e.g., 1 mg/kg, 5 mg, kg, 10 mg/kg, 20 mg/kg, 30 mg/kg, 40 mg/kg, 50 mg/kg, 60 mg/kg, 70 mg/kg, 80 mg/kg, 90 mg/kg or 100 mg/kg) administered s.c., once daily for 14 days Following the 14 day treatment period, subjects will be re-assessed according to the above criteria, with statistical analysis as described above.

Results—

It is expected that neuropathy subjects administered D-Arg-2'6'-dimethyltyrosine-Lys-Phe-NH$_2$ for a period of 14 days will report a reduction in hyperalgesia symptoms compared to subjects administered no treatment or a vehicle-only placebo. The reduction in hyperalgesia will be manifest in improved scoring for touch and sharpness detection thresholds, grooved pegboard tests, and thermal detection tests compared to control subjects.

These results will show that aromatic-cationic peptides of the present technology, such as D-Arg-2'6'-dimethyltyrosine-Lys-Phe-NH$_2$ are useful in the treatment of vincristine-induced hyperalgesia, and drug-induced hyperalgesia generally. The results will show that the methods and compositions described herein are useful in the treatment of drug-induced peripheral neuropathy or hyperalgesia.

Example 3—Use of D-Arg-2'6'-dimethyltyrosine-Lys-Phe-NH$_2$ in the Treatment of Hyperalgesia in Humans This example will demonstrate use of the methods and compositions of the present technology in the treatment of hyperalgesia. The example will demonstrate the use of D-Arg-2'6'-dimethyltyrosine-Lys-Phe-NH$_2$ in the treatment of hyperalgesia associated with peripheral neuropathy of various etiologies in humans.

Patients will be recruited to the study as they present in clinic with chronic (>6 months' duration), spontaneous, ongoing, neuropathy-related pain. Independent studies will address neuropathies resulting from, caused by, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. Subjects will be selected such that they have a single type of neuropathy and no known risk factors for neuropathy types outside the scope of the study in which the subject is enrolled. Those enrolled will rate their daily maximum level of pain at 4 or greater on a visual analog scale (VAS). Subjects will be screened for their willingness to enroll in the study, and informed consent will be obtained. Healthy subjects will also be recruited for collection of comparison data.

After a focused interview about the medical history, the patient will be asked to describe sensory symptoms by choosing from a list of ideal type word descriptors. Ongoing and daily maximum pain intensity will be rated on a VAS with prompts of "no pain" at the bottom and "most imaginable" at the top. The areas of pain and sensory disturbances will be drawn by each patient on a standardized body map. Neuropathy subjects are predicted to identify the following three zones of sensation:

a) The painful area: The zone of ongoing pain located on the tips of the fingers and/or toes. The tip of the index finger is expected to be involved in all patients and will be used as the test site in this zone.

b) The border area: Adjacent and proximal to, but distinct from the painful area, represented by nonpainful sensory disturbances and located in the palms and/or soles of the feet. The thenar eminence is expected to be involved in all patients and will be used as the test site in this zone.

c) The nonpainful area: Adjacent and proximal to, but distinct from the border area, reported by the patient to feel "normal." This site is expected to be always proximal to the wrists and/or ankles. Sensory testing will be conducted on the volar surface of the arm.

The tip of the index finger, thenar eminence, and volar forearm, will be tested in normal subjects for comparison. Patients will be specifically queried about the stimuli that provoked pain or caused an exacerbation of ongoing pain in these regions, including the effects that clothing, bed linens, bathing, and normal activities of daily living cause. Each zone will be examined for any physical changes, such as scaling, finger clubbing, and erythema, which will be documented. The areas of sensory disturbance will be physically probed by light touch with a camel hair brush and by manual massage to screen for the presence of allodynia or hyperalgesia.

Touch and Sharpness Detection Thresholds—

Touch detection thresholds will be determined with von Frey monofilaments using the up/down method as previously reported. Starting with a bending force of 0.02 g, each monofilament will be applied to a spot on the skin less than 2 mm in diameter for approximately one second. The force of the filament detected four consecutive times will be assigned as the touch detection threshold. Sharpness detection will be determined using weighted 30-gauge metal cylinders. Briefly, the tip of 30-gauge needles (200 mm diameter) will be filed to produce flat, cylindrical ends and the luers will be fitted to calibrated brass weights with the desired force (100, 200, and 400 mN) level for each stimulus. Each loaded needle will be placed inside a separate 10 cc syringe where it will be able to move freely. Each stimulus will be applied for one second perpendicular to the skin 10 times within each area of interest in a pseudorandom order. The subjects will indicate whether the stimulus is perceived as touch, pressure, sharp, or other. The percentages of each reply will be calculated and then combined into group grand means for comparison. The 50% sharpness detection threshold will be calculated as the weighted needle that caused five or more sharp responses after 10 consecutive stimuli.

Grooved Pegboard Test—

Manual dexterity will be assessed with the grooved pegboard test. Subjects will be instructed to fill a five-by-five slotted pegboard in an ordered fashion and the times for both dominant and non-dominant hands will be recorded Thermal Detection Thresholds—

The threshold for heat pain will be determined using the Marstock technique. A radiometer will be used at the outset of testing to ascertain the baseline skin temperature at all testing sites. All tests and measurements will be conducted at room temperature 22° C. Thermal ramps will be applied using a 3.6×3.6 cm Peltier thermode from a baseline temperature of 32° C. Skin heating will be at a ramp of 0.30° C./s, and skin cooling will be at a ramp of −0.5° C./s. Subjects will be instructed to signal when the stimulus is perceived as first becoming warmer and then painfully hot, or as first becoming cooler and then painfully cold. If a subject fails to reach a given threshold before the cutoff temperature of 51.5° C. for the ascending ramp or 3° C. held for 10 seconds in the cooling test, the cutoff values will be assigned for any that are not reached. The final threshold value for each skin sensation in each patient will be determined by averaging the results of three heating and cooling trials.

Statistical Analysis—

The thresholds for touch detection will be compared using nonparametric methods (Wilcoxon's test). The sharpness detection, thermal thresholds, and times in the grooved pegboard tests will be compared using analysis of variance and post hoc comparison of the means with Duncan's multiple range tests. Comparisons of mechanical and thermal thresholds will be performed between healthy subjects and patients for the different areas of the tested skin. Further analyses will be performed between glabrous and volar skin within the patient group. For every comparison performed in the present study, $p<0.05$ will be considered significant.

Following initial assessment of the above criteria, subjects will be divided into four groups:
a) Healthy controls
b) No treatment
c) Vehicle-only placebo, administered s.c., once daily for 14 days
d) D-Arg-2'6'-dimethyltyrosine-Lys-Phe-NH$_2$ at 1-100 mg/kg (e.g., 1 mg/kg, 5 mg/kg, kg, 10 mg/kg, 20 mg/kg, 30 mg/kg, 40 mg/kg, 50 mg/kg, 60 mg/kg, 70 mg/kg, 80 mg/kg, 90 mg/kg or 100 mg/kg) administered s.c., once daily for 14 days Following the 14 day treatment period, subjects will be re-assessed according to the above criteria, with statistical analysis as described above.

Results—

It is expected that neuropathy subjects administered D-Arg-2'6'-dimethyltyrosine-Lys-Phe-NH$_2$ for a period of 14 days will report a reduction in hyperalgesia compared to subjects administered a vehicle-only placebo. The reduction in hyperalgesia will be manifest in improved scoring for touch and sharpness detection thresholds, grooved pegboard tests, and thermal detection tests compared to control subjects.

These results will show that aromatic-cationic peptides of the present technology, such as D-Arg-2'6'-dimethyltyrosine-Lys-Phe-NH$_2$, are useful in the treatment of neuropathy-related hyperalgesia generally.

Example 4—Use of D-Arg-2'6'-dimethyltyrosine-Lys-Phe-NH$_2$ in the Prevention of Hyperalgesia in Humans This example will demonstrate use of the methods and compositions of the present technology in the prevention of hyperalgesia. The example will demonstrate the use of D-Arg-2'6'-dimethyltyrosine-Lys-Phe-NH$_2$ in the prevention of hyperalgesia associated with peripheral neuropathy of various etiologies in humans.

Subjects at risk for developing hyperalgesia will be recruited as they present in clinic for the treatment of conditions associated with the development of peripheral neuropathy or hyperalgesia. Independent studies will address neuropathy and hyperalgesia resulting from, caused by, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. Subjects will be selected such that they are at risk for developing a single type of neuropathy or hyperalgesia, having no risk factors outside the scope of the study in which the subject is enrolled, and as yet not having symptoms associated with neuropathy or hyperalgesia. Subjects will be screened for their willingness to enroll in the study, and informed consent will be obtained. Healthy subjects will also be recruited for collection of comparison data.

After a focused interview about the medical history, baseline measurements of touch and sharpness detection thresholds, grooved pegboard tests, and thermal detection thresholds will be determined according to the methods described above, with statistical analysis as described above.

Following initial assessment of the above criteria, subjects will be divided into four groups:
a) Healthy controls
b) No treatment
c) Vehicle-only placebo, administered s.c., once daily
d) D-Arg-2'6'-dimethyltyrosine-Lys-Phe-NH$_2$ at 1-100 mg/kg (e.g., 1 mg/kg, 5 mg/kg, kg, 10 mg/kg, 20 mg/kg, 30 mg/kg, 40 mg/kg, 50 mg/kg, 60 mg/kg, 70 mg/kg, 80 mg/kg, 90 mg/kg or 100 mg/kg) administered s.c., once daily Subjects will be evaluated weekly during the trial for sharpness detection thresholds, grooved pegboard tests, and thermal detection thresholds. The trial will continue for a period of 28 days, or until the no-treatment and placebo control groups display hyperalgesia according to the above criteria, at which point subjects will undergo a final assessment.

Results—

It is expected that subjects at risk of developing neuropathy or hyperalgesia administered D-Arg-2'6'-dimethyltyrosine-Lys-Phe-NH$_2$ will show attenuated development of neuropathy or hyperalgesia compared to untreated and placebo controls.

These results will show that aromatic-cationic peptides of the present technology, such as D-Arg-2'6'-dimethyltyrosine-Lys-Phe-NH$_2$, are useful in the prevention of neuropathy and hyperalgesia generally. The results will show that the methods and compositions described herein are useful in the prevention of neuropathy or hyperalgesia generally.

The present technology is not to be limited in terms of the particular embodiments described in this application, which are intended as single illustrations of individual aspects of the present technology. Many modifications and variations of the present technology can be made without departing from its spirit and scope, as will be apparent to those skilled in the art. Functionally equivalent methods and compositions within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All references cited herein are incorporated herein by reference in their entireties and for all purposes to the same extent as if each individual publication, patent, or patent application was specifically and individually incorporated by reference in its entirety for all purposes.

Other embodiments are set forth within the following claims.

What is claimed is:

1. A method for treating peripheral neuropathy or hyperalgesia in a subject in need thereof, comprising administering to the subject an effective amount of a peptide having the formula Phe-D-Arg-Phe-Lys-NH$_2$.

2. The method of claim 1, wherein the peripheral neuropathy or hyperalgesia is drug-induced.

3. The method of claim 2, wherein the drug is a chemotherapeutic agent.

4. The method of claim 3, wherein the chemotherapeutic agent is procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, thioguanine, or vincristine.

5. The method of claim 3, wherein the chemotherapeutic agent is vincristine.

6. The method of claim 2, wherein the peptide is administered simultaneous with the drug.

7. The method of claim 2, wherein the peptide is administered subsequent to the drug.

8. The method of claim 1, wherein the peripheral neuropathy causes hyperalgesia.

9. The method of claim 1, wherein the subject is a human.

10. The method of claim 1, wherein the peptide is administered intravenously, orally, subcutaneously, transdermally, intraperitoneally, intrathecally intramuscularly, intranasally, bucally, sublingually, translingually, or topically.

11. A method for reducing the occurrence of hyperalgesia in a subject in need thereof, comprising administering to the subject an effective amount of a peptide having the formula Phe-D-Arg-Phe-Lys-NH$_2$.

12. The method of claim 11, wherein the hyperalgesia is drug-induced.

13. The method of claim 12, wherein the drug is a chemotherapeutic agent.

14. The method of claim 13, wherein the chemotherapeutic agent is procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, thioguanine, or vincristine.

15. The method of claim 13, wherein the chemotherapeutic agent is vincristine.

16. The method of claim 12, wherein the peptide is administered simultaneous with the drug.

17. The method of claim 12, wherein the peptide is administered subsequent to the drug.

18. The method of claim 11, wherein the peptide is administered prior the onset of hyperalgesia.

19. The method of claim 11, wherein the subject is a human.

20. The method of claim 11, wherein the peptide is administered intravenously, orally, subcutaneously, transdermally, intraperitoneally, intrathecally intramuscularly, intranasally, bucally, sublingually, translingually, or topically.

* * * * *